US011730715B2

(12) United States Patent
Holzer et al.

(10) Patent No.: US 11,730,715 B2
(45) Date of Patent: Aug. 22, 2023

(54) CONSUMABLE COMPOSITIONS AND METHODS OF PRODUCING THE SAME

(71) Applicant: Nuka Enterprises, Henderson, CO (US)

(72) Inventors: Erin Holzer, Henderson, CO (US); Peter Barsoom, Henderson, CO (US); Justin Kirkland, Henderson, CO (US)

(73) Assignee: Nuka Enterprises, Henderson, CO (US)

( * ) Notice: Subject to any disclaimer, the term of this patent is extended or adjusted under 35 U.S.C. 154(b) by 0 days.

(21) Appl. No.: 16/987,103

(22) Filed: Aug. 6, 2020

(65) Prior Publication Data

US 2021/0038560 A1 Feb. 11, 2021

Related U.S. Application Data

(60) Provisional application No. 62/883,619, filed on Aug. 6, 2019.

(51) Int. Cl.

| | | |
|---|---|---|
| *A61K 31/352* | (2006.01) | |
| *A61K 31/05* | (2006.01) | |
| *A61K 36/185* | (2006.01) | |
| *A61K 36/66* | (2006.01) | |
| *A61K 36/61* | (2006.01) | |
| *A61K 31/522* | (2006.01) | |
| *A61K 9/00* | (2006.01) | |
| *A61K 36/9062* | (2006.01) | |
| *A61K 36/41* | (2006.01) | |
| *A61K 31/198* | (2006.01) | |
| *A61K 36/53* | (2006.01) | |
| *A61K 31/4415* | (2006.01) | |
| *A61K 36/575* | (2006.01) | |
| *A61K 36/81* | (2006.01) | |

(52) U.S. Cl.
CPC .......... *A61K 31/352* (2013.01); *A61K 9/0056* (2013.01); *A61K 31/05* (2013.01); *A61K 31/198* (2013.01); *A61K 31/4415* (2013.01); *A61K 31/522* (2013.01); *A61K 36/185* (2013.01); *A61K 36/41* (2013.01); *A61K 36/53* (2013.01); *A61K 36/575* (2013.01); *A61K 36/61* (2013.01); *A61K 36/66* (2013.01); *A61K 36/81* (2013.01); *A61K 36/9062* (2013.01)

(58) Field of Classification Search
CPC .................................................. A61K 9/0056
See application file for complete search history.

(56) References Cited

U.S. PATENT DOCUMENTS

| | | | | |
|---|---|---|---|---|
| 8,642,645 B2 * | 2/2014 | Kelly | ...................... | A61K 31/35 514/454 |
| 9,474,725 B1 | 10/2016 | Reillo et al. | | |
| 9,839,612 B2 | 12/2017 | Reillo et al. | | |
| 9,972,680 B2 | 5/2018 | Reillo et al. | | |
| 9,974,739 B2 | 5/2018 | Reillo et al. | | |
| 10,084,044 B2 | 9/2018 | Reillo et al. | | |
| 10,103,225 B2 | 10/2018 | Reillo et al. | | |
| 2004/0081664 A1 | 4/2004 | Gow et al. | | |
| 2008/0057161 A1 * | 3/2008 | Brucker | ..................... | A23F 5/00 426/73 |
| 2010/0015261 A1 * | 1/2010 | Frank | ..................... | A61K 36/18 424/764 |
| 2016/0220593 A1 | 8/2016 | Anastassov et al. | | |
| 2016/0346339 A1 | 12/2016 | Finley et al. | | |
| 2017/0172977 A1 * | 6/2017 | Kleidon | ............... | A61K 31/352 |
| 2017/0290870 A1 * | 10/2017 | Schaneville | ......... | A61K 36/185 |
| 2018/0125980 A1 * | 5/2018 | Finley | .................... | A61K 47/22 |

OTHER PUBLICATIONS

"High Love" (I Tried Cannabis-Infused Sex Chocolate | High Love Review, The Stoner Mom, Feb. 14, 2018) (Year: 2018).*
"High Love ingredients" (wheresweed.com, downloaded in Feb. 2021) (Year: 2021).*
"Libido Secret" (Amazon.com, first available in Mar. 31, 2017) (Year: 2017).*
Baggott et al (Psychopharmacology of theobromine in healthy volunteers, Psychopharmacology (Berl). Jul. 2013 ; 228(1): 109-118 ) (Year: 2013).*
Cernilton (Efficacy Study of a Standardized Pollen Extract Preparation (Cernilton) to Treat Inflammatory Chronic Prostatitis-Chronic Pelvic Pain Syndrome (CP-CPPS), first posted date Jun. 12, 2009) (Year: 2009).*
"Bliss" (Edibles Review | Bliss Peanut Butter Cups, the Stoner Mom, Mar. 30, 2018) (Year: 2018).*
"Bliss Ingredients" (wheresweed.com, downloaded in Feb. 2021) (Year: 2021).*
Talbott et al (Effect of Magnolia officinalis and Phellodendron amurense (Relora®) on cortisol and psychological mood state in moderately stressed subjects, Journal of the International Society of Sports Nutrition 2013, 10:37) (Year: 2013).*
Nell et al (A Randomized, Double-Blind, Parallel-Group, Placebo-Controlled Trial of Extract Sceletium tortuosum (Zembrin) in Healthy Adults, The Journal of Alternative and Complementary Medicine, vol. 19, No. 11, 2013, pp. 898-904) (Year: 2013).*
Kimura et al (L-Theanine reduces psychological and physiological stress responses, Biological Psychology 74 (2007) 39-45). (Year: 2007).*
"Midnight" (Edibles Review | Midnight by 1906 | Chocolate for Effortless Sleep, publication date Dec. 15, 2017) (Year: 2017).*
"Corydalis" (PeaceHealth, last review date Mar. 24, 2015) (Year: 2015).*

(Continued)

*Primary Examiner* — Mark V Stevens
*Assistant Examiner* — Alparslan Asan
(74) *Attorney, Agent, or Firm* — McDonnell Boehnen, Hulbert & Berghoff LLP

(57) ABSTRACT

The disclosure provides compositions comprising cannabinoids and active ingredients and/or excipients and methods of producing the compositions.

21 Claims, No Drawings

(56) References Cited

OTHER PUBLICATIONS

"Go" (Edibles Review | Go! Energy Chocolate for Slaying the Day, the Stoner Mom, publication date Nov. 23, 2017) (Year: 2017).*
"Go Ingredients" (wheresweed.com, downloaded in Feb. 2021) (Year: 2021).*
"Caffeine" (Healthline, Helen West, updated on Sep. 27, 2017) (Year: 2017).*
Kolangi et al. (Effect of Alpinia officinarum Hance rhizome extract on spermatogram factors in men with idiopathic infertility: A prospective double-blinded randomised clinical trial, Andrologia, publication date Oct. 31, 2018) (Year: 2018).*
Mark Cropley, The Effects of Rhodiola rosea L. Extract on Anxiety, Stress, Cognition and Other Mood Symptoms, Phytother. Res. 29: 1934-1939 (Year: 2015).*
Tatimah Peth-Nui, Effects of 12-Week Bacopa monnieri Consumption on Attention, Cognitive Processing,Working Memory, and Functions of Both Cholinergic andMonoaminergic Systems in Healthy Elderly Volunteers, Evidence-Based Complementary and Alternative Medicine, vol. 2012, Article ID 606424 (Year: 2012).*
Jamie Witherby, Magnesium Glycinate: Supplement Guide, HVMN Blog (Year: 2019).*
Corey Whelan, Does Chocolate Have Caffeine?, healthline (Year: 2018).*
Wang Jia Bei et al, L-Tetrahydropalamatine: A Potential New Medication for the Treatment of Cocaine Addiction, Future Med Chem. Feb. 2012 (Year: 2012).*
DHH-B, Tringali Vibrant Health, downloaded in Nov. 2021 (Year: 2021).*
The National Academies Press, Institute of Medicine, Dietary Reference Intakes for Thiamin, Riboflavin, Niacin, Vitamin B6, Folate, Vitamin B12, Pantothenic Acid, Biotin, and Choline. Washington, DC: The National Academies Press, publication date: 1998 (Year: 1998).*
Li Chao-Wu et al, Determination of L-tetrahydropalmatine in human plasma by HPLC and pharmacokinetics of its disintegrating tablets in healthy Chinese, Eur J Drug Metab Pharmacokinet (2011) 36:257-262 (Year: 2011).*
Tailor Made Compounding, Peptide Catalog, publication date: Aug. 5, 2019 (Year: 2019).*
Coetzee et al., "High-mesembrine Sceletium extract (Trimesemine™) is a monoamine releasing agent, rather than only a selective serotonin reuptake inhibitor", J Ethnopharmacol, 177: 111-6, (Jan. 2016), Epub Nov. 2015.
Grotenhermen, "Pharmacokinetics and pharmacodynamics of cannabinoids", Clin. Pharmacokinet, 42(4):327-60, (Sep. 2003).
Harvey et al., "Pharmacological actions of the South African medicinal and functional food plant Sceletium tortuosum and its principal alkaloids", J Ethnopharmacol, 137(3):1124-9, (Oct. 2011), Epub Jul. 2011.
Huestis, "Human cannabinoid pharmacokinetics", Chem Biodivers, 4(8):1770-804, (Aug. 2007).
Marcenac et al., "Effect of I-tetrahydropalmatine on dopamine release and metabolism in the rat striatum", Psychopharmacology (Berl), 89(1):89-93, (May 1986).
Maruyama et al., "Confirmation of the anxiolytic-like effect of dihydrohonokiol following behavioural and biochemical assessments", J Pharm Pharmacol, 53(5):721-5, (May 2001).
Nobre et al., "L-theanine, a natural constituent in tea, and its effect on mental state", Asia Pac. J Clin Nutr, 17 Suppl 1:167-8, (Jan. 2008).
Pellati et al., "*Cannabis sativa* L. and NonpsychoactiveCannabinoids: Their Chemistry and Role against Oxidative Stress, Inflammation, and Cancer", Biomed Res. Int., 2018:1691428, pp. 1-15, (Dec. 2018).
Russo, "Taming THC: potential cannabis synergy and phytocannabinoid-terpenoid entourage effects" Br J Pharmacol, 163(7):1344-64, (Aug. 2011).
Wang et al., "I-tetrahydropalamatine: a potential new medication for the treatment of cocaine addiction", Future Med Chem, 4(2):177-86, (Feb. 2012).
International Search Report issued by International Searching Authority for International Application No. PCT/US2020/045226 dated Oct. 27, 2020 (2 pages).
Written Opinion issued by International Searching Authority for International Application No. PCT/US2020/045226 dated Oct. 27, 2020 (8 pages).

* cited by examiner

CONSUMABLE COMPOSITIONS AND METHODS OF PRODUCING THE SAME

CROSS REFERENCE TO RELATED APPLICATIONS

This application claims priority to U.S. Provisional Patent Application Ser. No. 62/883,619, filed Aug. 6, 2019, the contents of which is hereby incorporated by reference in its entirety.

BACKGROUND OF DISCLOSURE

Field

The disclosure provides consumable compositions comprising cannabinoids and one or more active ingredients and/or excipients and methods of producing the compositions.

Technical Background

*Cannabis sativa* contains over 400 chemical compounds, of which more than 60 of them are phytocannabinoid compounds. Cannabidiol (CBD) and delta-9-tetrahydrocannabinol (Δ9-THC) are the most prevalent and best known. THC is responsible for the psychoactive effects associated with cannabis consumption, along with analgesic and immunomodulatory properties, while CBD is non-psychoactive but still known to be a modulator of the body's endogenous endocannabinoid system.

CBD has also been reported to possess anti-anxiety, anti-inflammatory, anti-psychotic, anticonvulsant, neuroprotective antioxidant, and antibiotic properties. In the presence of Δ9-THC, CBD is able to antagonize CB1 at low concentration mitigating adverse effects like tachycardia, anxiety, sedation, and hunger associated with Δ9-THC (Pellati et al. (2018) *Biomed Res. Int*., pp. 1-15). Combining THC and CBD together in various ratios can ultimately determine the physiologic effect.

There are many challenges in creating a reproducible effect when consuming cannabis, including bioavailability, taste, and onset time. Cannabinoids are highly lipophilic molecules with very low aqueous solubility and bioavailability. It is estimated that only 3-10% are absorbed from the digestive tract when consumed orally compared to 30% when inhaled via smoking or vaporization. A variety of factors, such as recent eating (for oral), depth of inhalation, how long breath is held for, and vaporizer temperature (for inhalation) all affect cannabinoid absorption, which can vary from 20-30% for oral administration and up to 10-60% for inhalation (Grotenhermen (2003) *Clin. Pharmacokinet*, 42(4):327-60).

Another challenge associated with oral consumption of cannabis is taste, which can limit consumer acceptance and likability of orally consumed products. Cannabis contains bitter constituents such as terpenes and flavonoids that impart a bitter and earthy taste. These compounds may be removed, but some efficacy may be lost as there have been synergistic effects reported for THC with terpenes and other phytocannabinoids (Russo, EB (2011) *Br J Pharmacol,* 163(7):1344-64). For this reason, a full spectrum cannabis extract may be preferred but formulators may want to mask the bitterness or create flavor profiles that complement it.

Cannabis-related effects or a feeling of being "high" generally manifest within a few minutes of the first inhalation (smoked or vaporized). The onset peaks after 10 minutes and may be maintained at a steady state for 3-5 hours in accordance with the plasma levels of THC. The pharmacokinetics (PK) profile of CBD is very similar to that of THC, whether it is administered orally, intravenously or inhaled. These pharmacokinetics (rapid onset, short time peak effect, and intermediate lasting effects) occur because first passage metabolism is avoided (PMID: Huestis, MA (2007) *Chem Biodivers,* 4(8):1770-804).

Most orally consumed cannabinoids have low reach maximal plasma concentrations after 60-120 minutes, although this can take even longer (up to 6 hours) and can be delayed. Extensive first-pass liver metabolism further reduces the oral bioavailability of THC.

Thus, there is a need for cannabis-based formulations to improve solubility, bioavailability, taste, and onset time. Described herein are compositions that can be consumed by ingestion, particularly through food products or tablets and capsules, with a quick onset time that can help improve or affect a variety of conditions, such as improving mood, reducing social anxiety, increasing energy, promoting sleep and relaxation, enhancing sexual arousal or experience, improving mental focus, and enhancing women's health.

BRIEF SUMMARY

The present disclosure relates to consumable compositions comprising cannabinoids and/or active ingredients, and methods of producing the same.

One aspect of the present disclosure provides a composition comprising tetrahydrocannabinol (THC) and cannabidiol (CBD) in a balanced ratio of about 1:1 to a ratio of about 1:6 and one or more active ingredients.

In some embodiments of the disclosure, the amount of THC in the composition is about 1 mg to about 50 mg and the amount of CBD in the composition is about 1 mg to about 50 mg.

In some embodiments of the disclosure, the one or more active ingredients is selected from the group consisting of L-theanine, theobromine, Sceletium tortuosum, and dihydrohonokiol, corydalis, theobromine, muira puama, catuaba, damiana, ashwaghanda, flower pollen, alpinia galanga, caffeine, rhodiola, bacopa, melatonin, passion flower, valerian root, 5-Hydroxytryptophan (5-htp), gamma-aminobutyric acid (GABA), chaste berry, cramp bark/black hawk, magnesium glycinate, potassium chloride, vitamin B6, and/or yohimbe.

In other embodiments of the disclosure, the amount of THC is about 1 mg to about 25 mg and the amount of CBD is from about 1 mg to about 25 mg, and wherein the active ingredients comprises L-theanine in an amount of about 50 mg to about 200 mg, theobromine in an amount of 50 mg to 200 mg, Sceletium tortuosum in an amount of about 5 mg to about 30 mg, and dihydrohonokiol in an amount of about 2.5 mg to about 25 mg. In some embodiments, the composition does not contain L-theanine.

In other embodiments of the disclosure, the amount of THC is about 1 mg to about 25 mg and the amount of CBD is from about 1 mg to about 25 mg, and wherein the one or more active ingredient comprises corydalis in an amount of about 30 mg to about 100 mg, and L-theanine in an amount of about 50 mg to about 200 mg.

In other embodiments of the disclosure, the amount of THC is about 1 mg to about 25 mg and the amount of CBD is from about 1 mg to about 25 mg, and wherein the one or more active ingredient comprises dihydrohonokiol in an amount of about 2.5 mg to about 25 mg, and L-theanine in an amount of about 50 mg to about 300 mg.

In other embodiments of the disclosure, the amount of THC is about 1 mg to about 25 mg and the amount of CBD is from about 1 mg to about 25 mg, and wherein the one or more active ingredient comprises theobromine in an amount of about 50 mg to about 300 mg, muira puama in an amount of about 50 mg to about 200 mg, catuaba in an amount of about 25 mg to about 150 mg, damiana in an amount of about 10 mg to about 100 mg, ashwaghanda in an amount of about 1 mg to about 600 mg, and flower pollen in an amount of about 1 mg to about 20 mg.

In other embodiments of the disclosure, the amount of THC is about 1 mg to about 25 mg and the amount of CBD is from about 1 mg to about 25 mg, and wherein the one or more active ingredient comprises alpinia galanga in an amount of about 50 mg to about 300 mg, theobromine in an amount of about 25 mg to about 200 mg, caffeine in an amount of about 30 mg to about 90 mg, L-theanine in an amount of about 60 mg to about 180 mg.

In other embodiments of the disclosure, the amount of THC is about 1 mg to about 25 mg and the amount of CBD is from about 1 mg to about 25 mg, and wherein the one or more active ingredient comprises alpinia galanga in an amount of about 50 mg to about 500 mg, bacopa in an amount of about 50 mg to about 500 mg, rhodiola in an amount of about 50 mg to about 300 mg, theobromine in an amount of about 25 mg to about 100 mg, caffeine in an amount of about 20 mg to about 60 mg, and L-theanine in an amount of about 40 mg to about 120 mg.

In some embodiments of the disclosure, the amount of THC is about 2.5 mg to about 7.5 mg and the amount of CBD is from about 5 mg to about 25 mg, wherein the one or more active ingredient comprises chaste berry in an amount of about 10 mg to about 40 mg, cramp bark/black hawk in an amount of about 10 mg to about 40 mg, magnesium glycinate in an amount of about 75 mg to about 150 mg, potassium chloride in an amount of about 25 mg to about 75 mg, and vitamin B6 in an amount of about 1 mg to about 2 mg, and wherein the composition further comprises CBG in an amount of about 2.5 mg to about 7.5 mg.

In some embodiments of the disclosure, the amount of THC is about 2.5 mg to about 7.5 mg and the amount of CBD is from about 5 mg to about 25 mg, wherein the one or more active ingredient comprises cramp bark/black hawk in an amount of about 10 mg to about 40 mg, THP in an amount of about 50 mg to about 150 mg, DHH magnolia extract in an amount of about 5 mg to about 10 mg, and vitamin B6 in an amount of about 1 mg to about 2 mg, and wherein the composition further comprises CBG in an amount of about 2.5 mg to about 7.5 mg.

In some embodiments of the disclosure, the total amount of the mixture of cannabinoids (e.g., THC, CBD, and/or CBG), and/or the active ingredients is about 100 mg to about 800 mg.

In some embodiments of the disclosure, the composition is contained in a food product, capsule, tablet, orally disintegrating tablet, pill, gummy, soft chew, beverage, tincture, mint, lozenge, pastille, lollipop, chewing gum, effervescent tablet, powder, or liquid.

In some embodiments of the disclosure, the food product is a chocolate, such as a dark chocolate, a milk chocolate, a white chocolate, a chocolate peanut butter cup, a chocolate covered coffee bean, or a chocolate gem.

In some embodiments of the disclosure, the composition is contained in a delivery vehicle to improve the solubility, bioavailability and onset time of the composition, wherein the delivery vehicle is a liposome, nanoparticle, complexation agent, cosolvency agent, a micelle, a nanocapsule, or a microcapsule.

In some embodiments of the disclosure, the composition further comprises a complexing substrate.

In some embodiments of the disclosure, the composition is low in sugar or sugar free.

In other embodiments of the disclosure, the composition further comprises a natural flavoring agent, an artificial flavoring agent, a bitter masker, a natural colorant, an artificial colorant, a binder, an emulsifier, a disintegrant, a sweetener, or a preservative.

Another aspect of the present disclosure provides an orally disintegrating tablet comprising tetrahydrocannabinol (THC) and cannabidiol (CBD) in a ratio of about 1:1 to a ratio of about 1:6 and one or more of excipients and flavoring agents.

Yet another aspect of the present disclosure provides, a method of preparing a food product or a tablet containing the composition comprising THC and cannabidiol CBD in a ratio of about 1:1 to a ratio of about 1:6 and one or more active ingredients, the method comprising: (i) combining the THC, CBD, and active ingredients with the food product or the tablet; and (ii) sheering and blending the total ingredients from step (i) to obtain a consumable composition.

DETAILED DESCRIPTION

The inventors have discovered new consumable compositions containing cannabinoids (e.g., THC, CBD, or CBG) that have improved bioavailability, taste, and onset time. For the purposes of promoting an understanding of the principles of the present disclosure, reference will now be made to specific embodiments and specific language will be used to describe the same.

Definitions:

Articles "a" and "an" are used herein to refer to one or to more than one (i.e. at least one) of the grammatical object of the article. By way of example, "an element" means at least one element and can include more than one element.

As used herein, the term "and/or" includes any and all combinations of one or more of the associated listed items. It will be further understood that the use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a percentage range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The term "about" in association with a numerical value means that the numerical value can vary plus or minus by 5% or less of the numerical value.

The term "cannabinoid" as used herein means any chemical substance that acts upon a cannabinoid receptor. For example the term cannabinoid includes, but is not limited to, cannabinoid ligands such as agonists, partial agonists, inverse agonists, or antagonists, as demonstrated by binding studies and functional assays. Cannabinoids can be derived from their respective 2-carboxylic acids (2-COOH) by decarboxylation (catalyzed by heat, light, or alkaline conditions). Cannabinoids include, but are not limited to, tetrahydrocannabinol (THC), tetrahydrocannabinolic acid (THCA), cannabidiol (CBD), cannabidiolic acid (CBDA), cannabinol (CBN), tetrahydrocannabivarin (THCV), cannabigerol (CBG), cannabichromene (CBC), cannabicyclol (CBL), cannabivarin (CBV), cannabidivarin (CBDV), cannabichromevarin (CBCV), cannabigerovarin (CBGV), cannabigerol monomethyl ether (CBGM), cannabielsoin (CBE), cannabicitran (CBT), and other major and minor phytocannabinoids.

Cannabinoids (e.g., CBD, CBG, and THC) can be obtained using a variety of extraction solvents, including supercritical carbon dioxide ($CO_2$) extraction, ethanol, hydrocarbon, water or any method known to those skilled in the art. The extract can be assayed before addition to the desired delivery format to ensure desired dose in finished product.

In some embodiments, the compositions comprise, for example, a balanced ratio of cannabinoids (e.g., THC to CBD). The term "balanced ratio" as used herein refers to a ratio of ingredients (e.g., cannabinoids or other active ingredients) that have similar amounts such that the mass is about equal or that the potency of the ingredients are about equal. The term balanced ratio as used herein also refers to the amounts of ingredients (e.g., cannabinoids or other active ingredients) that result in a desired effect (e.g., mood or sleep enhancement). Examples of balanced ratios of cannabinoids (e.g., a ratio of THC to CBD, a ratio of CBD to THC, a ratio of THC to CBG, or a ratio of CBG to THC) as described herein can be about 0.8:1, 0.9:1. 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5.0, 1:5.1, 1:5.2, 1:5.3, 1:5.4, 1:5.5, 1:5.6, 1:5.7, 1:5.8, 1:5.9, 1:6, 1:6.1, or 1:6.2.

It will be understood that a balanced ratio of cannabinoids as used herein can refer to any combination of cannabinoids. For example, a balanced ratio of cannabinoids can be a 1:1.2 ratio of THC to CBD or a 1:1.2 ratio of CBD to THC. As other non-limiting examples, a composition having a balanced ratio of THC to CBD can comprise a mass of 5 mg of THC and 5 mg of CBD (e.g., a 1:1 ratio), 5 mg THC and 15 mg of CBD (e.g., a 1:3 ratio), 2.5 mg THC and 5 mg CBG (e.g., a 1:2 ratio), 2.5 mg of THC and 15 mg of CBD (e.g., a 1:6 ratio), or 5 mg THC and 5 mg CBG (e.g., a 1:1 ratio).

A ratio can refer to the ratio of cannabinoids in the target dose and not the input material. The ratio can also take into account the potency of each cannabinoid. For example, a composition of the disclosure containing a 1:1 ratio of THC to CBD (or, said another way, a 1:1 ratio of CBD to THC) can contain 10 mg of THC with a potency of 50% and 5.1 mg of CBD with a potency of 100%. As another non-limiting example, a composition having a balanced ratio of THC to CBD can comprise 40 mg of THC having 50% potency and 20.4 mg of CBD having 98% potency.

The compositions of the disclosure can contain a variety of active ingredients that are suitable for consumption, including, but not limited to cannabinoids (e.g., THC and CBD), L-theanine, theobromine, Sceletium tortuosum, dihydrohonokiol (magnolia bark extract), corydalis (L-tetrahydropalmatine), theobromine, herbal extracts (e.g., muira puama, catuaba, damiana, ashwaghanda, and flower pollen), alpinia galanga, caffeine, rhodiola, bacopa, melatonin, passion flower, valerian root, 5-Hydroxytryptophan (5-htp), gamma-aminobutyric acid (GABA), chaste berry, cramp bark/black hawk, magnesium glycinate, potassium chloride, vitamin B6, and yohimbe.

Corydalis is described in Wang et al. (2012) *Future Med Chem,* 4(2):177-86). Its primary active compound is L-tetrahydropalmatine (THP). (Marcenac et al. (1986) *Psychopharmacology,* 89(1):89-93).

L-theanine is a non-protein amino acid found almost solely in tea (Nobre et al. (2008) *Asia Pac. J Clin Nutr,* 260(6 Pt 1) 167-8).

Theobromine is a methylxanthine compound that is naturally present in chocolate.

Sceletium tortuosum, also known as kanna and sceletium tortuosum root extract, is a South African plant. The major active compounds are alkaloids, namely mesembrine and mesembrenone. (Harvey et al. (2011) *J Ethnopharmacol,* 137(3):1124-9, PMID: Coetzee et al. (2016) *J Ethnopharmacol,* 177:111-6).

Dihydrohonokiol (DHH) is a reduced derivative of honokiol, which is a compound from the bark of Magnolia plant species *Magnolia officinalis* and *Magnolia obovata* (Maruyama et al. (2001) *J Pharm Pharmacol,* 53(5):721-5).

Ashwagandha (*Withania somnifera*) is a popular herb in Ayurveda.

Damiana (Turnera aphrodisiaca) is described in the British Herbal Pharmacopoeia.

Alpinia galanga, also known galangal, greater galangal, Java galangal and Siamese ginger, is a member of the ginger family (P. N. Ravindran, I. Balachandran, in Handbook of Herbs and Spices, Volume 3, 2006). The extract used in the compositions of the disclosure can include a water-soluble, methyl eugenol—free extract and standardized for polyphenol-, polysaccharide-, and pyrocatecollic-type tannins.

Muira puama is a plant and includes both the wood and root.

Catuaba is an herb.

The tablet containing compositions of the disclosure can be a pressed tablet that can be prepared by tableting methods known in the art. For example, a tablet (also referred to herein as a drop) can be prepared from a powder or granule mixture, filling a dye mold, and then compressing and ejecting the mixture. Tablets can be pressed into various shapes (e.g., round, oblong, teardrop, or asymmetrical) and sizes. Tablets can also have a variety of physical features, such as they can be large or small in diameter, flat or convex, scored or unscored, imprinted with a symbol, letters, or numbers, and have one or more colors (e.g., red, blue, orange, yellow, purple, pink, black, grey, or green tablets, or multicolor tablets). The tablets can be, for example, swallowable, chewable, or orally dissolvable.

In some embodiments, the tablets can be an orally disintegrating tablet or an orally dissolving tablet (ODT). Orally disintegrating tablets can quickly dissolve or disintegrate in the mouth without water when placed on or under a subject's tongue. In some embodiments, the orally dissolving tablet can dissolve in the mouth in about 1 minute or less.

In some embodiments, the compositions of the disclosure can be contained in a capsule. Examples of capsules include, but are not limited to, hard capsules, soft capsules, and embedded capsules. Capsules can be prepared by methods known in the art. A hard capsule can be prepared on manual, semi-automatic, or automatic capsule filling machines. A hard capsule can contain, for example, two pieces that fit together that can be filled with a formulation (e.g., a powder or miniature pellets). A soft capsule can be prepared by filling at the same time it is produced and sealed on an automatic machine. A soft capsule can contain, for example, a liquid formulation (e.g., ingredients dissolved or suspended in oil or other liquid). An embedded capsule can have a composition embedded in the capsule shell matrix to allow more than one composition to be delivered using the same capsule. Capsules can be gelatin capsules made of collagen or vegetable capsules made of cellulose (e.g., hydroxypropyl methyl cellulose). Capsules can also have a variety of physical features, such as they can be large or small in diameter, round, oval, oblong, or diamond shaped, imprinted with a symbol, letters, or numbers, and have one or more colors (e.g., red, blue, orange, yellow, purple, pink, black, grey, or green capsules, or multicolor capsules).

In addition to the cannabinoids and active ingredients described herein, the compositions of the disclosure can contain a variety of additional ingredients or excipients. Excipients refer to ingredients that are formulated along with active ingredients of the composition for the purpose of improving characteristics of the composition (e.g., stability or flavor). Categories of excipients include, but are not limited to, antiadherents, binders, coatings, coloring agent, complexing substrate, disintegrants, flavoring agents, lubricants, preservatives, sorbents, sweeteners, and delivery vehicles. It will be appreciated that certain ingredients can fall under multiple categories of excipients. For example, magnesium sterate can be used as an antiadherent ingredient and as a lubricant ingredient.

Excipients that can be used in the compositions of the disclosure include, but are not limited to, dextrose, anhydrous dibasic calcium phosphate, crospovidone, povidone, croscarmellose sodium, vegetarian magnesium stearate, colloidal silicon dioxide, sodium starch glycolate, hypromellose, microcrystalline cellulose, D-mannitol, and polyvinyl acetate.

A filler can include, but is not limited to lactose, starch, dextrose, sucrose, fructose, maltose, mannitol, sorbitol, kaolin, microcrystalline cellulose, powdered cellulose or any combination of the foregoing. The filler can consist of a mixture of water soluble fillers to reduce the chance of unpleasant grittiness for orally dissolvable tablets. The filler can also be a direct compression sugar such as confectioners' sugar, dextrates, dextrin, dextrose, fructose, isomalt, maltose, mannitol, polydextrose, sorbitol, or other sugars and sugar derivatives.

The compositions of the disclosure can include antiadherents, which can prevent the formulation to sticking to, for example, tablet punches. Magnesium stearate is an example of an antiadherent ingredient.

The compositions of the disclosure can include a flavoring agent. Flavoring agents can include, but are not limited to, natural flavoring agents, artificial flavoring agents, fruit extracts, bitter maskers, natural colorants, artificial colorants, binders, emulsifiers, disintegrants, sweeteners (e.g., stevia, sucralose, monk fruit, erythritol, xylitol, or yacon syrup), savory agents, preservatives.

The compositions can contain a disintegrant. Disintegrants can expand and dissolve when wet causing the tablet to break apart and dissolve (e.g., in the mouth or in the digestive tract). Examples of disintegrants include, but are not limited to, cross-linked polymers (e.g., crospovidone) or cross-linked sodium carboxymethyl celluous (croscarmellose sodium).

The compositions of the disclosure can comprise a binder. Examples of binders can include disaccharides (e.g., sucrose or lactose), polysaccharides (e.g., starches or cellulose), sugar alcohols (e.g., xylitol, sorbitol, or mannitol), gelatin, or synthetic polymers (e.g., polyvinylpyrrolidone (PVP) or polyethylene glycol (PEG)).

The compositions of the disclosure can comprise a coloring agent. Examples of coloring agents include, but are not limited to, titanium dioxide, riboflavin, carmine extract, brown iron oxide, blue 2, yellow 5, and azo dyes.

The compositions of the disclosure can contain a complexing substrate, which can be an ingredient having a long chain fatty acid or a medium chain fatty acid. Examples of a complexing substrate include, but are not limited to, vegetable, nut, or seed oils (such as coconut oil, peanut oil, soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (such as fish liver oil, shark oil and mink oil).

The compositions of the disclosure can comprise a lubricant. Lubricants prevent the ingredients from clumping together and from sticking to, for example, tablet punches. Examples of lubricants can include talc or silica, and fats (e.g. vegetable stearin, magnesium stearate or stearic acid). Lubricants can be hydrophilic or hydrophobic (e.g., magnesium stearate).

The compositions of the disclosure can include preservatives. Examples of preservatives include, but are not limited to, antioxidants (e.g., vitamin A, vitamin E, vitamin C, retinly palmitate, rosemary extract, and selenium), amino acids (e.g., cysteine and methionine), citric acid, sodium citrate, and parabens (e.g., methyl paraben or propyl paraben).

The compositions of the disclosure can be low in sugar, sugar free. Sugar substitutes include, but are not limited to, stevia, monk fruit, sucralose, mannitol, maltitol, sorbitol, and xylitol.

The compositions of the disclosure have improved solubility, bioavailability, and onset time. Various formulation technologies can be applied to improve solubility, bioavailability and onset time. These technologies can involve packaging the composition in a delivery vehicle. Delivery vehicles include, but are not limited to, encapsulation in lipid-based formulations (e.g., liposomes) and nanoparticles, complexation (e.g., cyclodextrins), cosolvency (e.g., ethanol, propylene glycol, PEG400, etc.), micellization (e.g., polysorbate 80, cremophor ELP etc.), and (nano)-(micro)-emulsification.

A patented microencapsulation technology by Lexaria called DehydraTECH™ (U.S. Pat. Nos. 9,474,725; 9,839,612; 9,974,739; 9,972,680; 10,103,225; and 10,084,044, all incorporated herein by reference) can be used in the products containing the compositions of the disclosure to allow for enhanced performance across taste, smell, bioavailability and onset time. The application of the technology involves mixing the beneficial compound of interest as a delivery "payload" together with certain fatty acids, infusing the mixture into a substrate material, and then using controlled dehydration synthesis processing to conjugate the payload and fatty acids together at a molecular level before integrating the newly-combined molecules into production.

The compositions of the disclosure can be delivered through oral, sublingual, pulmonary, buccal, dermal, topical, or transdermal administration routes. The compositions can be administered through eating, swallowing, dissolving in the mouth, drinking, inhalation, smoking, topical applications. Forms can include: chocolate, capsule, tablet, ODT, pill, gummy (pectin or gelatin), soft chew, beverage, tincture, mint, lozenge, pastille, lollipop, chewing gum, effervescent tablet, powder, or liquid.

The compositions of the disclosure can be combined with and delivered in the form of a food product (e.g., chocolate, coffee bean, or mint), a tablet, capsule, tincture, beverage, gummy, orally dissolving tablet, pastille, vape pen, topical gel, patch, or cream.

The chocolate can be a solid chocolate, a chocolate peanut butter cup, liquid chocolate, filled chocolate, coated (e.g., coffee bean or fruit piece), or other chocolate. The chocolate can be dark chocolate, milk chocolate, white chocolate, or infused chocolate.

A gummy can be gelatin or pectin based. A pectin-based gummy can contain roughly 34% sugar, 34% water, 29% corn syrup, 1.2% pectin, 1.2% citric acid, 0.6% sodium citrate and color and flavor as needed for taste and desired appearance. A gelatin-based gummy can contain roughly 38% sugar, 25% water, 30% corn syrup, 6.1% gelatin, and color and flavor as needed for taste and desired appearance. In both gelatin and pectin gummies, the active ingredients can be added after the cooking step to minimize the effects of heat exposure.

In some embodiments, the compositions can contain about a 1:1 ratio to about a 1:6 ratio of cannabinoids in combination with active ingredients including, but not limited to, L-theanine, theobromine, Sceletium tortuosum, dihydrohonokiol, and/or magnolia bark extract. In some embodiments, the composition does not contain L-theanine (suntheanine). The product can be formulated to encourage a positive mood and reduce social anxiety. The amount of active ingredients delivered per serving can range depending on dosage form. The L-theanine dose can range from 50 mg to 200 mg (e.g., from 50 mg to 100 mg, 80 mg to 100 mg, 90 to 110 mg, or 100 mg to 150 mg), the theobromine dose can range from 50 mg to 150 mg (e.g., from 50 mg to 100 mg, 80 mg to 110 mg, or 90 mg to 140 mg), Sceletium tortuosum dose can range from 5 mg to 30 mg (e.g., from 10 mg to 20 mg, 15 mg to 25 mg, or 18 mg to 22 mg), dihydrohonokiol (magnolia bark extract) dose can range from 2.5 mg to 25 mg (e.g., from 5 mg to 10 mg, 7 mg to 10 mg, or 5 mg to 15 mg), the dose of THC can range from 1 mg to 25 mg (e.g., from 1 mg to 5 mg, 5 mg to 10 mg, 5 mg to 20 mg, or 1 mg, 2 mg, 2.5 mg, 5 mg, 7.5 mg, 10 mg, 15 mg, 20 mg, or 25 mg), and the dose of CBD from 1 mg to 25 mg (e.g., from 1 mg to 5 mg, 5 mg to 10 mg, 5 mg to 20 mg, or 1 mg, 2 mg, 2.5 mg, 5 mg, 7.5 mg, 10 mg, 15 mg, 20 mg, or 25 mg). In some embodiments, the composition can further comprise anhydrous dibasic calcium phosphate, calcium carbonate, microcrystalline cellulose, sodium starch glycolate, croscarmellose sodium, povidone, crosspovidone, hydroxypropyl methylcellulose, vegetarian magnesium stearate, colloidal silicon dioxide, vegetarian stearic acid, hypromellose, glycerin, riboflavin (color), carmine extract (color), and/or titanium dioxide (color), or combinations thereof. Cannabinoid compositions of the disclosure having some or all of these ingredients and doses can be referred to herein as Bliss (see Example 1).

In some embodiments, the composition can contain about a 1:1 ratio to about a 1:6 ratio of cannabinoids in combination with active ingredients including, but not limited to L-theanine, and/or an extract of corydalis (L-tetrahydropalmatine). The product can be formulated to promote sleep, helping users fall asleep quickly and wake up refreshed. The amount of active ingredients delivered per serving can range depending on dosage form. The corydalis extract dose can range from 30 mg to 150 mg (e.g., from 40 mg to 120 mg, 40 mg to 60 mg, 80 mg to 140 mg, or 90 mg to 110 mg), the dose of L-theanine can range from 50 mg to 200 mg (e.g., from 50 mg to 150 mg, 80 mg to 120 mg, or 90 mg to 110 mg), the dose of THC from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg), and the dose of CBD can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg). In some embodiments, the composition can further comprise microcrystalline cellulose, anhydrous dibasic calcium phosphate, calcium carbonate, sodium starch glycolate, croscarmellose sodium, crosspovidone, povidone, vegetarian magnesium stearate, hypromellose, hydroxypropyl methylcellulose, silicon dioxide, glycerin, blue 2 (e.g., FD&C Blue No. 2 lake), carmine extract (color), and/or titanium dioxide (color) or combinations thereof. Cannabinoid compositions having some or all of these ingredients and doses can be referred to herein as Midnight (see Example 2).

In some embodiments, the composition can contain about a 1:1 ratio to about a 1:6 ratio of cannabinoids in combination with active ingredients including, but not limited to dihydrohonokiol (magnolia bark extract), and/or L-theanine. The product can be formulated to promote a state of mental calm and relaxation. The amount of active ingredients delivered per serving can range depending on dosage form. The dihydrohonokiol dose can range from 2 mg to 25 mg (e.g., 2 mg to 10 mg, 5 mg to 8 mg, or 5 mg to 20 mg), the dose of L-theanine can range from 50 mg to 300 mg (e.g., from 50 mg to 100 mg, 80 mg to 110 mg, 100 mg to 150 mg, 150 mg to 200 mg, 180 mg to 210 mg, or 100 mg to 200 mg), the dose of THC can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg), and the dose of CBD can range from 1 mg to 25 mg (e.g., from 1 mg to 5 mg, 5 mg to 10 mg, 5 mg to 20 mg, or 15 mg to 25 mg, or 1 mg, 2 mg, 2.5 mg, 5 mg, 7.5 mg, 10 mg, 15 mg, 20 mg, or 25 mg). In some embodiments, the composition can further comprise anhydrous dibasic calcium phosphate, calcium carbonate, crospovidone, croscarmellose sodium, crosspovidone, povidone, vegetarian magnesium stearate, hypromellose, microcrystalline cellulose, hydroxypropyl methylcellulose, silicon dioxide, glycerin, blue 2 (color), titanium dioxide (color), or combinations thereof. Cannabinoid compositions of the disclosure having some or all of these ingredients and doses can be referred to herein as Chill (see Example 3).

In some embodiments, the composition can contain about a 1:1 ratio to about a 1:6 ratio of cannabinoids in combination with active ingredients including, but not limited to theobromine, herbal extracts of muira puama, catuaba, damiana, ashwaghanda and/or flower pollen. The product can be formulated to enhance sexual function and stimulate sexual arousal in both men and women. The amount of active ingredients delivered per serving can range depending on dosage form. The theobromine dose may range from 50 mg to 250 mg (e.g., from 50 mg to 150 mg, 150 mg to 200 mg, 180 mg to 220 mg, or 190 mg to 210 mg), the muira puama dose can range from 50 mg to 200 mg (e.g., 80 mg to 160 mg, 130 mg to 160 mg, 50 mg to 150 mg, or 180 mg to 200 mg), the catuaba dose can range from 25 mg to 150 mg (e.g., from 50 mg to 100 mg, 60 mg to 90 mg, 80 mg to 110 mg, or 150 mg to 200 mg), the damiana dose can range from 10 mg to 100 mg (e.g., from 30 mg to 50 mg, 50 mg to 80 mg, 70 mg to 80 mg, or 50 mg to 100 mg), the ashwaghanda dose can range from 1 mg to 600 mg, (e.g., 1 mg to 160 mg, 1 mg to 10 mg, 50 mg to 200 mg, 130 mg to 160 mg, 200 mg to 400 mg, 280 mg to 320 mg, 250 mg to 550 mg, or 550 mg to 600 mg) the flower pollen dose can range from 1 mg to 20 mg (e.g., 1 mg to 5 mg, 5 mg to 15 mg, or 5 mg to 20 mg), the THC dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg), and the CBD dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg). In some embodiments, the composition can further comprise dextrose, anhydrous dibasic calcium phosphate, croscarmellose sodium, microcrystalline cellulose, crospovidone, colloidal silicon dioxide, calcium carbonate, dextrose, vegetarian stearic acid, copovidone, povidone, vegetarian magnesium stearate, sodium starch glycolate, hydroxypropyl methylcellulose, hypromellose, microcrystalline cellulose, glycerin, brown iron oxide (color), carmine extract (color), and/or titanium dioxide (color), or combinations thereof. Cannabinoid compositions of the disclosure having these ingredients and doses can be referred to herein as Love (see Example 4).

In some embodiments, the composition can contain about a 1:1 ratio to about a 1:6 ratio of cannabinoids in combination with active ingredients including, but not limited to alpinia galanga, L-theanine, caffeine and/or theobromine. The product can be formulated to deliver physical energy and mental focus. The amount of active ingredients delivered per serving can range depending on dosage form. The alpinia galanga dose can range from 50 mg to 350 mg (e.g., 50 mg to 200 mg, 150 mg to 200 mg, 225 mg to 275 mg, or 250 mg to 300 mg), the theobromine dose can range from 25 mg to 200 mg (e.g., 50 mg to 125 mg, 80 mg to 110 mg, or 150 mg to 200 mg), the caffeine dose can range from 30 mg to 150 mg (e.g. 30 mg to 90 mg, 50 mg to 100 mg, 60 mg to 90 mg, or 80 mg to 140 mg), the L-theanine dose can range from 60 mg to 180 mg (e.g., 50 to 150 mg, 80 mg to 120 mg, 100 to 150 mg, or 90 mg to 170 mg), the THC dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg), and the CBD dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg). In some embodiments, the composition can further comprise anhydrous dibasic calcium phosphate, calcium carbonate, crosspovidone, croscarmellose sodium, vegetarian stearic acid, povidone, vegetarian magnesium stearate, colloidal silicon dioxide, sodium starch glycolate, hypromellose, microcrystalline cellulose, hydroxypropyl methylcellulose, glycerin, blue 1, yellow 5 (e.g., FD&C Yellow No. S lake), and/or titanium dioxide (color), or combinations thereof. Cannabinoid compositions of the disclosure having these ingredients and doses can be referred to herein as Go (see Example 5).

In some embodiments, the composition can contain about a 1:1 ratio to about a 1:6 ratio of cannabinoids in combination with active ingredients including, but not limited to rhodiola, bacopa, alpinia galanga, L-theanine, caffeine, and/or theobromine. The product can be formulated to deliver and enhance mental focus. The amount of active ingredients delivered per serving can range depending on dosage form. The rhodiola dose can range from about 50 mg to about 300 mg (e.g., from 50 mg to 100 mg, 150 mg to 250 mg, 175 mg to 275 mg, or 150 mg to 300 mg), the alpinia galanga dose can range from 50 mg to 600 mg (e.g., from 50 mg to 300 mg, 100 mg to 300 mg, 250 mg to 500 mg, or 230 mg to 260 mg), the bacopa dose can range from 50 mg to 600 mg (e.g., from 50 mg to 180 mg, 140 mg to 170 mg, 150 mg to 350 mg, or 280 mg to 320 mg), the theobromine dose can range from 25 mg to 100 mg (e.g., from 25 mg to 50 mg, 50 mg to 90 mg, 65 mg to 85 mg, or 50 mg to 100 mg), the caffeine dose can range from 20 mg to 60 mg (e.g., from 20 mg to 50 mg, 30 mg to 50 mg, or 30 mg to 60 mg), the L-theanine dose can range from 40 mg to 120 mg (e.g., from 50 mg to 100 mg, 60 mg to 90 mg, or 60 mg to 110 mg), the THC dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg), and the CBD dose can range from 1 mg to 25 mg (e.g., from 1 mg to 5 mg, 5 mg to 10 mg, or 5 mg to 20 mg, or 1 mg, 2 mg, 2.5 mg, 5 mg, 7.5 mg, 10 mg, 15 mg, 20 mg, or 25 mg). In some embodiments, the composition can further comprise anhydrous dibasic calcium phosphate, calcium carbonate, crospovidone, povidone, vegetarian magnesium stearate, colloidal silicon dioxide, sodium starch glycolate, hypromellose, hydroxypropyl methyl cellulose, microcrystalline cellulose, glycerin, riboflavin (color), carmine extract (color), and/or titanium dioxide (color), or combinations thereof. Cannabinoid compositions of this disclosure having these ingredients and doses can be referred to herein as Genius (see Example 6).

In some embodiments, the composition can contain about a 1:1 ratio to about a 1:6 ratio of cannabinoids (e.g., a ratio of THC to CBD, CBD to THC, CBD to CBG, CBG to CBD, THC to CBG, or CBG to THC, or combinations of ratios thereof) in combination with active ingredients including, but not limited to chaste berry, cramp bark/black hawk, magnesium glycinate, potassium chloride, vitamin B6, THP, and/or DHH magnolia extract. In some embodiments, the composition comprises a combination of cannabinoids (e.g., THC, CBD, and CBG) and a combination of active ingredients that can comprise chaste berry, cramp bark/black hawk, magnesium glycinate, potassium chloride, and vitamin B6. In some embodiments, the composition comprises a combination of cannabinoids (e.g., THC, CBD, and CBG) and a combination of active ingredients that can comprise cramp bark/black hawk, THP, DHH magnolia extract, and vitamin B6. The product can be formulated for women's menstrual health. The amount of active ingredients delivered per serving can range depending on dosage form. The chaste berry dose can range from 5 mg to 25 mg (e.g., from 5 mg to 20 mg, 10 mg to 20 mg, 10 mg to 15 mg, or 15 mg to 25 mg), the cramp bark/black hawk dose can range from 10 mg to 40 mg (e.g., from 10 mg to 30 mg, 10 mg to 20 mg, 20 mg to 40 mg, or 15 mg to 25 mg), the magnesium glycinate dose can range from 75 mg to 150 mg (e.g., from 75 mg to 125 mg, 75 mg to 100 mg, 90 mg to 110 mg, or 100 mg to 150 mg), the potassium chloride dose can range from 25 mg to 75 mg (e.g., from 25 mg to 50 mg, 30 mg to 50 mg, 30 mg to 60 mg, or 50 mg to 75 mg), the vitamin B6 dose can range from 1 mg to 2 mg (e.g., 1 mg or 2 mg), the THP dose can range from 50 mg to 150 mg (e.g., 50 mg to 100 mg, 75 mg to 100 mg, 80 mg to 110 mg, 100 mg to 125 mg, or 100 mg to 150 mg), the DHH magnolia extract dose can range from 5 mg to 10 mg (e.g., from 5 mg to 7.5 mg, 7.5 mg to 10 mg, or 5.5 mg to 8.5 mg) THC dose can range from 2.5 mg to 7.5 mg (e.g., from 2.5 mg to 5.5 mg, or 5.5 mg to 7.5 mg, or 2.5 mg, 3.0 mg, 3.5 mg. 4.0 mg, 4.5 mg, 5.0 mg, 5.5 mg, 6.0 mg, 6.5 mg, or 7.5 mg), the CBD dose can range from 5 mg to 25 mg (e.g., from 5 mg to 10 mg, or 5 mg to 20 mg, or 5 mg, 7.5 mg, 10 mg, 15 mg, 20 mg, or 25 mg), and the CBG dose can range from 2.5 mg to 7.5 mg (e.g., from 2.5 mg to 5.5 mg, or 5.5 mg to 7.5 mg, or 2.5 mg, 3.0 mg, 3.5 mg. 4.0 mg, 4.5 mg, 5.0 mg, 5.5 mg, 6.0 mg, 6.5 mg, or 7.5 mg). In some embodiments, the composition can further comprise one or more excipients, flavoring agents, and/or combinations thereof. Cannabinoid compositions of this disclosure having these ingredients and doses can be referred to herein as Lunar (see Example 7).

In some embodiments, the composition is an ODT formula that can contain about a 1:1 ratio to about a 1:6 ratio of cannabinoids in combination with one or more excipients. In some embodiments, the ODT formula comprises a THC dose that can range from 1 mg to 5 mg (e.g., from 1 mg to 5 mg, 2.5 mg to 3.5 mg, 2 mg to 5 mg, or 1 mg to 3 mg, or 1 mg, 1.5 mg, 2 mg, 2.5 mg, 3 mg, 3.5 mg, 4 mg, 4.5 mg, or 5 mg) and a CBD dose that can range from 1 mg to 5 mg (e.g., from 1 mg to 5 mg, 2.5 mg to 3.5 mg, 2 mg to 5 mg, or 1 mg to 3 mg, or 1 mg, 1.5 mg, 2 mg, 2.5 mg, 3 mg, 3.5 mg, 4 mg, 4.5 mg, or 5 mg). The excipients can include, but are not limited to, D-mannitol, crospovidone, polyvinyl acetate, isomalt, a sweetener, a flavoring agent, and magnesium stearate, or combinations thereof. In other embodiments, the ODT formula additionally contains one or more active ingredients. In some embodiments, the ODT formula comprises Lexaria technology.

Another aspect of the present disclosure provides a method of preparing a food product or tablet containing the composition comprising THC and CBD in a ratio of about 1:1 or a ratio of about 1:6 and one or more active ingredients, the method comprising: (i) combining the THC, CBD, and active ingredients with the food product or tablet; and (ii) sheering and blending the total ingredients from step (i) to obtain a consumable composition.

Another aspect of the present disclosure provides all that is disclosed and illustrated herein.

The following examples are offered by way of illustration and not by way of limitation.

EXAMPLE 1

Mood Enhancing and Anxiety Reducing Compositions

The Bliss compositions were formulated to encourage a positive mood and reduce social anxiety. Tables 1-6 describe the ingredients of example compositions of the disclosure.

TABLE 1

Bliss 20 mg Peanut Butter Cup Formula #1

| Ingredient | Target dose (mg) | Potency (NLT) | Input Amount (mg) | Approximate Percent of total |
|---|---|---|---|---|
| L-Theanine (Suntheanine) | 100 | 100% | 100 | 35% |
| Theobromine | 100 | 100% | 100 | 35% |
| Sceletium - IPA:W | 13 | 100% | 13 | 5% |
| Sceletium - Tri5 | 7 | 100% | 7 | 2% |
| Dihydrohonokiol (DHH) | 7.5 | 100% | 7.5 | 3% |
| THC (from CO2 cannabis extract) | 20 | 50% | 40 | 14% |
| CBD isolate | 20 | 98% | 20.4 | 7% |
| Total Blend Dosage (mg) | | | 288 | |

TABLE 2

Bliss 20 mg Peanut Butter Cup Formula #2

| Ingredient | Target dose (mg) | Potency (NLT) | Input Amount (mg) | Approximate Percent of total |
|---|---|---|---|---|
| Theobromine | 100 | 100% | 100 | 53% |
| Sceletium - IPA:W | 13 | 100% | 13 | 7% |
| Sceletium - Tri5 | 7 | 100% | 7 | 4% |
| Dihydrohonokiol (DHH) | 7.5 | 100% | 7.5 | 24% |
| THC (from CO2 cannabis extract) | 20 | 50% | 40 | 22% |
| CBD isolate | 20 | 98% | 20.4 | 11% |
| Total Blend Dosage (mg) | | | 188 | |

TABLE 3

Bliss 5 mg Dark Chocolate/Milk Chocolate Peanut Butter Cup Formula #1

| Ingredient | Target dose (mg) | Potency (NLT) | Input Amount (mg) | Approximate Percent of total |
|---|---|---|---|---|
| L-Theanine (Suntheanine) | 100 | 100% | 100 | 41% |
| Theobromine | 100 | 100% | 100 | 41% |
| Sceletium - IPA:W | 13 | 100% | 13 | 5% |
| Sceletium - Tri5 | 7 | 100% | 7 | 3% |
| Dihydrohonokiol (DHH) | 7.5 | 100% | 7.5 | 3% |
| THC (from CO2 cannabis extract) | 5 | 50% | 10 | 4% |
| CBD isolate | 5 | 98% | 5.1 | 2% |
| Total Blend Dosage (mg) | | | 243 | |

TABLE 4

Bliss 5 mg Dark Chocolate/Milk Chocolate Peanut Butter Cup Formula #2

| Ingredient | Target dose (mg) | Potency (NLT) | Input Amount (mg) | Approximate Percent of total |
|---|---|---|---|---|
| Theobromine | 100 | 100% | 100 | 70% |
| Sceletium - IPA:W | 13 | 100% | 13 | 9% |
| Sceletium - Tri5 | 7 | 100% | 7 | 5% |
| Dihydrohonokiol (DHH) | 7.5 | 100% | 7.5 | 5% |
| THC (from CO2 cannabis extract) | 5 | 50% | 10 | 7% |
| CBD isolate | 5 | 98% | 5.1 | 4% |
| Total Blend Dosage (mg) | | | 143 | |

An example serving size for the Bliss chocolate cups is 1 piece.

Other ingredients for the Bliss chocolate cups can include: chocolate, peanut butter, peanut flower, powdered sugar, cocoa butter, mesquite flour, ghee, sugar, sea salt, sunflower oil, and rosemary extract.

TABLE 5

Bliss Drops Formulation #1

| Ingredient | Dose |
|---|---|
| L-Theanine | 100 mg |
| Theobromine | 100 mg |
| *Sceletium tortuosum* root extract | 20 mg |
| Cannabis extract (5 mg THC/5 mg CBD) | 10 mg |
| Magnolia bark extract (*Magnolia officinalis*) | 7.5 mg |
| Other Ingredients | |

Anhydrous Dibasic Calcium Phosphate, Microcrystalline Cellulose, Sodium Starch glycolate, Croscarmellose Sodium, Povidone, Contains 2% or less of: Vegetarian Magnesium Stearate, colloidal silicon dioxide, Vegetarian Stearic Acid, Hypromellose, Glycerin, Riboflavin (color), carmine extract (color), titanium dioxide (color).

TABLE 6

Bliss Drops Formulation #2

| Ingredient | Dose |
|---|---|
| Theobromine | 100 mg |
| *Sceletium tortuosum* root extract | 20 mg |
| Cannabis extract (5 mg THC/5 mg CBD) | 10 mg |
| Magnolia bark extract (*Magnolia officinalis*) | 7.5 mg |
| Other Ingredients | |

Calcium carbonate, silicon dioxide, microcrystalline cellulose, crosspovidone, magnesium stearate, hydroxypropryl methylcellulose, glycerine, titanium dioxide, carmine acid, riboflavin.

An example serving size for the Bliss drops is 1 tablet (0.75 g).

EXAMPLE 2

Sleep Enhancing Compositions

The Midnight compositions were formulated to promote sleep and help users fall asleep quickly and wake up refreshed. Tables 7-9 describe the ingredients of example compositions of the disclosure.

TABLE 7

Midnight 5 mg Gems

| Ingredient | Target dose per serving (mg) | Potency (NLT) | Input Amount (mg) | Approximate Percent of total |
|---|---|---|---|---|
| L-tetrahydropalmatine (THP) (corydalis rhizome extract) | 100 | 98% | 102 | 87% |
| THC (from CO2 cannabis extract) | 5 | 50% | 10 | 9% |
| CBD isolate | 5 | 98% | 5.1 | 4% |
| Total Blend Dosage (mg) | | | 117 | |

The Midnight 5 mg gems can also be made with the following ingredients: milk chocolate, sunflower oil, cannabis extract (5 mg THC and 5 mg CBD), and natural flavors. The Midnight 5 mg gems can be consumed by taking 1 piece at a time, for example.

TABLE 8

Midnight Drops Formulation #1

| Ingredient | Dose |
|---|---|
| L-Theanine | 100 mg |
| corydalis rhizome extract (*Corydalis yanhusuo*) | 50 mg |
| Cannabis extract (5 mg THC/5 mg CBD) | 10 mg |
| Other Ingredients | |

Microcrystalline Cellulose, Anhydrous Dibasic Calcium Phosphate, Sodium Starch glycolate, Croscarmellose Sodium, Povidone, Contains 2% or less of: Vegetarian Magnesium Stearate, Hypromellose, Glycerin, Blue 2, carmine extract (color), titanium dioxide (color).

TABLE 9

Midnight Drops Formulation #2

| Ingredient | Dose |
|---|---|
| Corydalis rhizome extract (*Corydalis yanhusuo*) | 100 mg |
| Cannabis extract (5 mg THC/5 mg CBD) | 10 mg |
| Other Ingredients | |

Calcium carbonate, silicon dioxide, microcrystalline cellulose, crosspovidone,, magnesium stearate, hydroxypropyl methylcellulose, glycerine, titanium dioxide, FD&C Blue No. 2 lake, carmine acid An example serving size for the Midnight drops is 1 tablet (0.75 g).

EXAMPLE 3

Compositions for Relaxation

The Chill compositions were formulated to promote a state of mental calm and relaxation. Tables 10-13 describe the ingredients of example chocolate gems containing an example composition of the disclosure.

TABLE 10

Chill 5 mg Gems Formulation #1

| Ingredient | Target dose per serving (mg) | Potency (NLT) | Input Amount (mg) | Approximate Percent of total |
|---|---|---|---|---|
| L-theanine (Suntheanine) | 200 | 100% | 200 | 87% |
| Dihydrohonokiol (DHH) (Magnolia bark extract) | 15 | 100% | 15 | 7% |
| THC (from CO2 cannabis extract) | 5 | 50% | 10 | 4% |
| CBD isolate | 5 | 98% | 5.1 | 2% |
| Total Blend Dosage (mg) | | | 230 | |

TABLE 11

Chill 5 mg Gems Formulation #2

| Ingredient | Target dose per serving (mg) | Potency (NLT) | Input Amount (mg) | Approximate Percent of total |
|---|---|---|---|---|
| L-theanine (Suntheanine) | 100 | 100% | 100 | 77% |
| Dihydrohonokiol (DHH) (Magnolia bark extract) | 15 | 100% | 15 | 12% |
| THC (from CO2 cannabis extract) | 5 | 50% | 10 | 8% |
| CBD isolate | 5 | 98% | 5.1 | 4% |
| Total Blend Dosage (mg) | | | 130 | |

The Chill 5 mg gems can be consumed by taking 1 piece at a time, for example.

Other ingredients for the Chill gems can include: milk chocolate, sunflower oil, and natural flavors.

TABLE 12

Chill Drops Formulation #1

| Ingredient | Dose |
|---|---|
| L-Theanine | 200 mg |
| Cannabis Extract (5 mg THC/25 mg CBD) | 30 mg |
| Magnolia Bark Extract (*Magnolia officinalis*) | 7.5 mg |
| Other Ingredients | |
| Anhydrous dibasic calcium phosphate, crospovidone, croscarmellose Sodium, Contains 2% or less of: povidone, vegetarian magnesium stearate, hypromellose, microcrystalline cellulose, glycerin, Blue 2 (color), titanium dioxide (color) | |

TABLE 13

Chill Drops Formulation #2

| Ingredient | Dose |
|---|---|
| L-Theanine | 100 mg |
| Cannabis extract (5 mg THC/25 mg CBD) | 30 mg |
| Magnolia bark extract (*Magnolia officinalis*) | 7.5 mg |
| Other Ingredients | |
| Calcium carbonate, silicon dioxide, microcrystalline cellulose, crosspovidone, magnesium stearate, hydroxypropyl methylcellulose, glycerine, titanium dioxide, FD&C Blue No. 2 Lake | |

An example serving size for the Chill Drops is 1 tablet (0.75 g).

EXAMPLE 4

Compositions to Enhance Sexual Arousal

The Love compositions were formulated to enhance sexual function and stimulate sexual arousal in both men and women. Tables 14-18 describe the ingredients of example compositions of the disclosure.

TABLE 14

Love 5 mg Beans

| Ingredient | Target dose per serving (mg) | Potency (NLT) | Input Amount (mg) | Approximate Percent of total |
|---|---|---|---|---|
| Theobromine | 200 | 100% | 200 | 33% |
| Muira puama | 150 | 100% | 150 | 25% |
| Catuaba | 100 | 50% | 200 | 33% |
| Damiana | 40 | 100% | 40 | 7% |
| Ashwaghanda (KSM66) | 1 | 100% | 1 | 1% |
| Flower Pollen | 1 | 100% | 1 | 1% |
| THC (from CO2 *cannabis* extract) | 5 | 50% | 10 | 2% |
| CBD isolate | 5 | 98% | 5.1 | 1% |
| Total Blend Dosage (mg) | | | 607 | |

The Love 5 mg beans can be consumed by taking two pieces (coffee beans) at a time, for example.

TABLE 15

Love 20 mg Beans

| Ingredient | Target dose per serving (mg) | Potency (NLT) | Input Amount (mg) | Approximate Percent of total |
|---|---|---|---|---|
| Theobromine | 200 | 100% | 200 | 31% |
| Muira puama | 150 | 100% | 150 | 23% |
| Catuaba | 100 | 50% | 200 | 31% |
| Damiana | 40 | 100% | 40 | 6% |
| Ashwaghanda (KSM66) | 1 | 100% | 1 | 1% |
| Flower Pollen (rye flower pollen extract) | 1 | 100% | 1 | 1% |
| THC (from CO2 *cannabis* extract) | 20 | 50% | 40 | 6% |
| CBD isolate | 20 | 98% | 20.4 | 3% |
| Total Blend Dosage (mg) | | | 652 | |

The Love 20 mg beans can be consumed by taking two pieces (coffee beans) at a time, for example.

Other ingredients for the Love beans can include: milk chocolate and natural flavors.

TABLE 16

Love 5 mg Gems

| Ingredient | Target dose per serving (mg) | Potency (NLT) | Input Amount (mg) | Approximate Percent of total |
|---|---|---|---|---|
| Theobromine | 200 | 100% | 200 | 33% |
| Muira puama | 150 | 100% | 150 | 25% |
| Catuaba | 100 | 50% | 200 | 33% |
| Damiana | 40 | 100% | 40 | 67% |
| Ashwaghanda (KSM66) | 1 | 100% | 1 | 1% |
| Flower Pollen | 1 | 100% | 1 | 1% |
| THC (from CO2 *cannabis* extract) | 5 | 50% | 10 | 2% |
| CBD isolate | 5 | 98% | 5.1 | 1% |
| Total Blend Dosage (mg) | | | 607 | |

The Love 5 mg gems can be consumed by taking 1 piece at a time, for example.

Other ingredients for the Love gems can include: milk chocolate, sunflower oil, and natural flavors.

TABLE 17

Love Drops Formulation #1

| Ingredient | Dose |
| --- | --- |
| Ashwagandha root extract (*Withania somnifera*) - KSM66 | 300 mg |
| Theobromine | 200 mg |
| Muira puama bark extract (*Ptychopetalum olacoides*) | 150 mg |
| Catuaba bark extract (*Erythroxylum Catuaba*) | 80 mg |
| Damiana leaf extract (*Turnera diffusa*) | 75 mg |
| *Cannabis* extract (2.5 mg THC/2.5 mg CBD) | 5 mg |
| Other Ingredients | |
| Dextrose, anhydrous dibasic calcium phosphate, croscarmellose sodium, microcrystalline cellulose, crospovidone, contains 2% or less of: colloidal silicon dioxide, vegetarian stearic acid, copovidone, povidone, vegetarian magnesium stearate, sodium starch glycolate, hypromellose, microcrystalline cellulose, glycerin, brown iron oxide (color), carmine extract (color), titanium dioxide (color). | |

TABLE 18

Love Drops Formulation # 2

| Ingredient | Dose |
| --- | --- |
| Ashwagandha root extract (*Withania somnifera*) - Sensoril | 150 mg |
| Theobromine | 200 mg |
| Muira puama bark extract (*Ptychopetalum olacoides*) | 150 mg |
| Catuaba bark extract (*Erythroxylum Catuaba*) | 100 mg |
| Damiana leaf extract (*Turnera diffusa*) | 40 mg |
| *Cannabis* extract (5 mg THC/5 mg CBD) | 10 mg |
| Other Ingredients | |
| Calcium carbonate, silicon dioxide, dextrose, crosspovidone,, microcrystalline cellulose, crosscarmellose sodium, sodium starch glycolate, magnesium stearate, hydroxypropyl methylcellulose, glycerine, titanium dioxide, iron oxide yellow, carmine acid | |

An example serving size for the Love drops is 2 tablets (1.5 g).

EXAMPLE 5

Compositions to Enhance Energy and Focus

The Go compositions were formulated to deliver physical energy and mental focus. Tables 19-23 describe the ingredients of example compositions of the disclosure.

TABLE 19

Go 1 mg Beans

| Ingredient | Target dose per serving (mg) | Potency (NLT) | Input Amount (mg) | Approximate Percent of total |
| --- | --- | --- | --- | --- |
| Alpinia galanga extract (EnXtra) | 300 | 100% | 300 | 48% |
| L-Theanine (Suntheanine) | 150 | 100% | 150 | 24% |
| Caffeine (coated) | 35 | 50% | 70 | 11% |
| Theobromine | 100 | 100% | 100 | 16% |
| THC (from CO2 *cannabis* extract) | 1 | 50% | 2 | 1% |
| CBD isolate | 1 | 98% | 1.0 | 1% |
| Total Blend Dosage (mg) | | | 623 | |

The Go 1 mg beans can be consumed by taking one bean at a time, for example.

TABLE 20

Go 5 mg Beans

| Ingredient | Target dose per serving (mg) | Potency (NLT) | Input Amount (mg) | Approximate Percent of total |
| --- | --- | --- | --- | --- |
| Alpinia galanga extract (EnXtra) | 300 | 100% | 300 | 43% |
| L-Theanine (Suntheanine) | 150 | 100% | 150 | 21% |
| Caffeine (coated) | 70 | 50% | 140 | 20% |
| Theobromine | 100 | 100% | 100 | 14% |
| THC (from CO2 *cannabis* extract) | 5 | 50% | 10 | 1% |
| CBD isolate | 5 | 98% | 5.1 | 1% |
| Total Blend Dosage (mg) | | | 705 | |

The Go 5 mg beans can be consumed by taking two beans at a time, for example.

Other ingredients in the beans can include: dark chocolate or milk chocolate, sunflower oil, and natural flavors.

TABLE 21

Go 5 mg Gems

| Ingredient | Target dose per serving (mg) | Potency (NLT) | Input Amount (mg) | Approximate Percent of total |
| --- | --- | --- | --- | --- |
| Alpinia galanga extract (EnXtra) | 300 | 100% | 300 | 39% |
| L-Theanine (Suntheanine) | 150 | 100% | 150 | 20% |
| Caffeine (coated) | 100 | 50% | 200 | 26% |
| Theobromine | 100 | 100% | 100 | 13% |
| THC (from CO2 *cannabis* extract) | 5 | 50% | 10 | 1% |
| CBD isolate | 5 | 98% | 5.1 | 1% |
| Total Blend Dosage (mg) | | | 765 | |

The Go gems can be consumed by taking 1 piece at a time, for example.

Other ingredients in the Go gems can include: chocolate, sunflower oil and natural flavors.

TABLE 22

Go Drops Formulation #1

| Ingredient | Dose |
| --- | --- |
| Greater galangal root extract (*Alpinia Galanga*) | 250 mg |
| L-Theanine | 120 mg |
| Theobromine | 100 mg |
| Caffeine | 80 mg |
| *Cannabis* extract (5 mg THC/5 mg CBD) | 10 mg |
| Other Ingredients | |

Anhydrous dibasic calcium phosphate, crospovidone, croscarmellose sodium, contains 2% or less of: vegetarian stearic acid, povidone, vegetarian magnesium stearate, colloidal silicon dioxide, sodium starch glycolate, hypromellose, microcrystalline cellulose, glycerin, Blue 1, Yellow 5, titanium dioxide (color).

TABLE 23

Go Drops Formulation #2

| Ingredient | Dose |
| --- | --- |
| Greater galangal root extract (*Alpinia Galanga*) | 175 mg |
| L-Theanine | 110 mg |
| Theobromine | 100 mg |
| Caffeine | 60 mg |
| *Cannabis* extract (5 mg THC/5 mg CBD) | 10 mg |
| Other Ingredients | |

Calcium carbonate, silicon dioxide, crosspovidone,, microcrystalline cellulose, sodium starch glycolate, magnesium stearate, hydroxypropyl methylcellulose, glycerine, titanium dioxide, FD&C Blue No. 1 Lake, FD&C Yellow No. 5 lake.

An example serving size for the Go drops is 1 tablet (0.75 g).

EXAMPLE 6

Compositions to Enhance Focus

The Genius compositions were formulated to deliver and enhance mental focus. Tables 24-25 describe the ingredients of example compositions of the disclosure.

TABLE 24

Genius Drops Formulation #1

| Ingredient | Dose |
| --- | --- |
| Greater Galangal root extract (*Alpinia Galanga*) | 300 mg |
| *Bacopa* whole herb extract (*Bacopa monnieri*) | 300 mg |
| *Rhodiola* root extract (*Rhodiola rosea*) | 250 mg |
| L-theanine | 80 mg |
| Theobromine | 75 mg |
| Caffeine | 40 mg |
| *Cannabis* extract (2.5 mg THC/2.5 mg CBD) | 5 mg |
| Other Ingredients | |

Anhydrous dibasic calcium phosphate, crospovidone, contains 2% or less of: povidone, vegetarian magnesium stearate, colloidal silicon dioxide, sodium starch glycolate, hypromellose, microcrystalline cellulose, glycerin, riboflavin (color), carmine extract (color), titanium dioxide (color).

TABLE 25

Genius Drops Formulation #2

| Ingredient | Dose |
| --- | --- |
| Greater Galangal root extract (*Alpinia Galanga*) | 250 mg |
| *Bacopa* whole herb extract (*Bacopa monnieri*) | 160 mg |
| *Rhodiola* root extract (*Rhodiola rosea*) | 250 mg |
| L-theanine | 80 mg |
| Theobromine | 75 mg |
| Caffeine | 40 mg |
| *Cannabis* extract (5 mg THC/5 mg CBD) | 10 mg |
| Other Ingredients | |

Calcium carbonate, silicon dioxide, crosspovidone,, microcrystalline cellulose, crosscarmellose sodium, sodium starch, starch glycolate, magnesium stearate, hydroxypropyl methyl cellulose, glycerine, titanium dioxide, riboflavin An example serving size for the Genius drops is 2 tablets (1.5 g).

EXAMPLE 7

Compositions for Women's Health

The Lunar compositions were formulated to support women's menstrual health. Tables 26-27 describe the ingredients of example compositions of the disclosure.

TABLE 26

Lunar Drops Formulation #1

| Ingredient | Dose |
| --- | --- |
| CBD | 15 mg |
| THC | 2.5 mg |
| CBG | 5 mg |
| Chaste berry | 20 mg |
| Cramp bark/black hawk | 20 mg |
| Magnesium glycinate | 100 mg |
| Potassium chloride | 50 mg |
| Vitamin B6 | 2 mg |

The Lunar drops of formulation #1 can be consumed by taking 1-2 drops daily.

TABLE 27

Lunar Drops Formulation #2

| Ingredient | Dose |
| --- | --- |
| CBD | 15 mg |
| THC | 2.5 mg |
| CBG | 5 mg |
| Cramp bark/black hawk | 20 mg |
| THP | 100 mg |
| DHH magnolia extract | 7.5 mg |
| Vitamin B6 | 2 mg |

The Lunar drops of formulation #2 can be consumed by taking 1 drop before going to sleep at night.

EXAMPLE 8

ODT Compositions

Table 28 describes the ingredients of orally disintegrating tablets (ODT) formulas of the disclosure. The ODT formulations described herein can utilize the fast acting Lexaria process.

TABLE 28

ODT Formulation

| Ingredient | Percent of total/amount |
| --- | --- |
| D-mannitol/crospovidone/polyvinyl acetate | 70-80% |
| Isomalt | 6-12% |
| Sweetener (e.g., stevia, splenda, monk fruit) | 0.1-1% |
| Flavor (e.g., natural, artificial, fruit extracts, sweet savory) | 1-6% |
| Magnesium Stearate | 0-2% |
| THC | 1-5 mg |
| CBD | 1-5 mg |

EXAMPLE 9

Onset Performance Study

An observational consumer use study was performed to compare the speed of onset performance, overall experience and palatability of THC and CBD infused chocolate formulations using Lexaria's palatability and absorption enabling technology (see U.S. Pat. Nos. 9,474,725; 9,839,612; 9,974,739; 9,972,680; 10,103,225; and 10,084,044, all incorporated herein by reference). A positive control formulation was used that used niacin rather than THC as a stimulant. Respondents recorded the time they consumed the product and the time that they began to feel effects of the product. Onset performance was calculated by subtracting the effect start time from the consumption time. The study confirmed that the time to onset on average was less than 20 minutes. It was concluded that use of sunflower oil, a long chain fatty acid, as a complexing substrate in the formulation served to influence intestinal uptake and lymphatic rather than hepatic distribution for more rapid systemic perfusion.

Any patents or publications mentioned in this specification are indicative of the levels of those skilled in the art to which the disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure is representative of preferred embodiments, are exemplary, and are not intended as limitations on the scope of the invention. Changes therein and other uses will occur to those skilled in the art which are encompassed within the spirit of the invention as defined by the scope of the claims. Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

It will be further understood that a number of aspects and embodiments are disclosed. Each of these has individual benefit and each can also be used in conjunction with one or more, or in some cases all, of the other disclosed aspects and embodiments, whether specifically delineated or not. Accordingly, for the sake of clarity, this description will refrain from repeating every possible combination of the individual aspects and embodiments in an unnecessary fashion. Nevertheless, the specification and claims should be read with the understanding that such combinations are implicitly disclosed, and are entirely within the scope of the disclosure and the claims, unless otherwise specified.

The invention claimed is:
1. A composition comprising:
   (a) tetrahydrocannabinol (THC) and cannabidiol (CBD) in a balanced ratio, wherein the THC is in an amount of about 1 mg to about 50 mg, the CBD is in an amount of about 1 mg to about 50 mg, and the THC:CBD ratio is 1:1 or 1:5; and
   (b) active ingredients comprising one of the following combinations:
      (i) theobromine in an amount of 50 mg to 200 mg, sceletium tortuosum in an amount of about 5 mg to about 30 mg, and dihydrohonokiol in an amount of about 2.5 mg to about 25 mg;
      (ii) dihydrohonokiol in an amount of about 2.5 mg to about 25 mg and L-theanine in an amount of about 80 mg to about 300 mg;
      (iii) theobromine in an amount of about 50 mg to about 300 mg, muira puama in an amount of about 50 mg to about 200 mg, catuaba in an amount of about 25 mg to about 150 mg, damiana in an amount of about 10 mg to about 100 mg, ashwaghanda in an amount of about 1 mg to about 600 mg, and flower pollen in an amount of about 1 mg to about 20 mg;
      (iv) alpinia galangal in an amount of about 50 mg to about 300 mg, theobromine in an amount of about 25 mg to about 200 mg, caffeine in an amount of about 30 mg to about 90 mg, and L-theanine in an amount of about 60 mg to about 180 mg; or
      (v) alpinia galangal in an amount of about 50 mg to about 500 mg, bacopa in an amount of about 50 mg to about 500 mg, rhodiola in an amount of about 50 mg to about 300 mg, theobromine in an amount of about 25 mg to about 100 mg, caffeine in an amount of about 20 mg to about 60 mg, and L-theanine in an amount of about 40 mg to about 120 mg, wherein the composition is a tablet, mint, lozenge, pastille, gummy, soft chew, beverage, tincture, lollipop, or chewing gum.

2. The composition of claim 1, wherein the THC is in an amount of about 1 mg to about 25 mg, the CBD is in an amount of about 1 mg to about 25 mg, and the active ingredients comprise combination (i).

3. The composition of claim 1, wherein the THC is in an amount of about 1 mg to about 25 mg, the CBD is in an amount of about 1 mg to about 25 mg, and further comprising L-tetrahydropalmatine in an amount of about 30 mg to about 100 mg.

4. The composition of claim 1, wherein the THC is in an amount of about 1 mg to about 25 mg, the CBD is in an amount of from about 1 mg to about 25 mg, and the active ingredients comprise combination (ii).

5. The composition of claim 1, wherein the THC is in an amount of about 1 mg to about 25 mg, the CBD is in an amount of from about 1 mg to about 25 mg, and the active ingredients comprise combination (iii).

6. The composition of claim 1, wherein the THC is in an amount of about 1 mg to about 25 mg, the CBD is in an amount of from about 1 mg to about 25 mg, and the active ingredients comprise combination (iv).

7. The composition of claim 1, wherein the THC is in an amount of about 1 mg to about 25 mg, the CBD is in an amount of from about 1 mg to about 25 mg, and the active ingredients comprise combination (v).

8. The composition of claim 1, wherein the total amount of the mixture of THC, CBD, and the active ingredients is about 100 mg to about 800 mg.

9. The composition of claim 1, wherein the tablet is an orally disintegrating tablet, an effervescent tablet, a chewable tablet, or a swallowable tablet.

10. The composition of claim 1, wherein the composition further comprises a delivery vehicle to improve the solubility, bioavailability and onset time of the composition, wherein the delivery vehicle is a liposome, a nanoparticle, a complexation agent, a cosolvency agent, a micelle, a nanocapsule, or a microcapsule.

11. The composition of claim 1, wherein the composition further comprises a complexing agent.

12. The composition of claim 1, wherein the composition is sugar free.

13. The composition of claim 1, wherein the composition further comprises a natural flavoring agent, an artificial flavoring agent, a fruit extract, a bitter masker, a natural colorant, an artificial colorant, a binder, an emulsifier, a disintegrant, a sweetener, or a preservative.

14. A method of preparing the composition of claim 1, the method comprising:
 (i) combining the THC, the CBD, and the active ingredients; and
 (ii) sheering and blending the total ingredients from step (i) to obtain a consumable composition.

15. A composition comprising:
 (a) about 1 mg to about 50 mg tetrahydrocannabinol (THC);
 (b) about 1 mg to about 50 mg cannabidiol (CBD);
 (c) cannabigerol (CBG); and
 (d) active ingredients comprising chaste berry in an amount of about 10 mg to about 40 mg, cramp bark/black haw in an amount of about 10 mg to about 25 mg, magnesium glycinate in an amount of about 75 mg to about 150 mg, potassium chloride in an amount of about 25 mg to about 75 mg, and vitamin B6 in an amount of about 1 mg to about 2 mg,
 wherein the composition is a tablet, mint, lozenge, pastille, gummy, soft chew, beverage, tincture, lollipop, chocolate, or chewing gum.

16. The composition of claim 15, wherein the THC is in an amount of about 1 mg to about 7.5 mg, the CBD is in an amount from about 5 mg to about 25 mg, and the CBG is in an amount of about 2.5 mg to about 7.5 mg.

17. The composition of claim 15, wherein the tablet is an orally disintegrating tablet, an effervescent tablet, a chewable tablet, or a swallowable tablet.

18. The composition of claim 15, wherein the chocolate is a dark chocolate, a milk chocolate, a white chocolate, a chocolate peanut butter cup, a chocolate covered coffee bean, or a chocolate gem.

19. The composition of claim 15, further comprising L-tetrahydropalmatine in an amount of about 30 mg to about 100 μg.

20. The composition of claim 15, further comprising cramp bark/black haw in an amount of about 10 mg to about 25 mg, L-tetrahydropalmatine in an amount of about 50 mg to about 150 mg, dihydrohonokiol in an amount of about 5 mg to about 10 mg, and vitamin B6 in an amount of about 1 mg to about 2 mg.

21. The composition of claim 16, further comprising L-tetrahydropalmatine in an amount of about 50 mg to about 150 mg.

* * * * *